United States Patent [19]
Wilson

[11] Patent Number: 5,830,138
[45] Date of Patent: Nov. 3, 1998

[54] INTRAVASCULAR CATHETER PROBE FOR CLINICAL OXYGEN, PH AND $CO_2$ MEASUREMENT

[75] Inventor: David F. Wilson, Philadelphia, Pa.

[73] Assignee: Trustees of the University of Pennsylvania, Philadelphia, Pa.

[21] Appl. No.: 767,305

[22] Filed: Dec. 16, 1996

[51] Int. Cl.$^6$ .................................................... A61B 5/00
[52] U.S. Cl. ............................. 600/327; 600/341; 436/68
[58] Field of Search ...................... 600/325, 327, 600/339, 341, 342; 436/68

[56] References Cited

U.S. PATENT DOCUMENTS

| | | |
|---|---|---|
| 3,787,119 | 1/1974 | Rybak . |
| 3,814,081 | 6/1974 | Mori . |
| 4,200,110 | 4/1980 | Peterson et al. . |
| 4,476,870 | 10/1984 | Peterson et al. . |
| 4,752,115 | 6/1988 | Murray, Jr. et al. . |
| 4,785,814 | 11/1988 | Kane . |
| 4,810,655 | 3/1989 | Khalil et al. ............................. 600/323 |
| 4,974,929 | 12/1990 | Curry ....................................... 600/342 |
| 5,012,809 | 5/1991 | Shulze . |
| 5,127,077 | 6/1992 | Iyer et al. ................................ 600/342 |
| 5,127,405 | 7/1992 | Alcala et al. . |
| 5,353,792 | 10/1994 | Lubbers et al. ......................... 600/311 |
| 5,408,999 | 4/1995 | Singh et al. ............................. 600/342 |
| 5,515,864 | 5/1996 | Zuckerman .............................. 600/311 |

*Primary Examiner*—Jennifer Bahr
*Assistant Examiner*—Eric F. Winakur
*Attorney, Agent, or Firm*—Duane, Morris & Heckscher LLP

[57] ABSTRACT

Methods and apparatus for the measurement of oxygen, pH and $CO_2$ in human and animal tissue is provided, in which the compounds preferably include a chromophore and/or fluorphor capable of absorbing an amount of energy and subsequently releasing the energy as phosphorescent and/or fluorescent light, and wherein the phosphorescence is quenched by molecular oxygen according to the Stern-Volmer relationship, $CO_2$ is measured by fluorphor which alters fluorescence with pH.

22 Claims, 2 Drawing Sheets

INTRAVASCULAR CATHETER PROBE FOR CLINICAL OXYGEN, PH AND CO₂ MEASUREMENT

FIELD OF THE INVENTION

The present invention is directed to catheters for oxygen, pH and $CO_2$ measurement in human and animal tissue, and in particular to catheters which are equipped with a microlight guide capable of exposing a solution of phosphorescent oxygen sensor and/or fluorescent pH sensor to measure oxygen by exciting and than collecting an amount of emitted light.

BACKGROUND OF THE INVENTION

Several sensor devices are known which are useful for measuring oxygen and pH content in human and animal tissues. For example, U.S. Pat. No. 4,758,814 describes such a device which is composed of an elongated flexible optical fiber containing a light sensing or light emitting end, and a light collecting and processing end. The light sensing end, which is adapted to be inserted into a human or animal body, i.e. a blood vessel, is composed of a portion of the optical fiber which is covered with a membrane, and which senses and returns light through the optical fiber to the light collecting and processing end which is, for example, a detector comprising photosensitive equipment such as a photomultiplier.

The membrane is constructed of a hydrophilic porous material containing a pH sensitive dye. Several hydrophobic microspheres are embedded in and carried by the membrane, each of which carries a fluorescent dye quenchable by oxygen. Light is supplied to the proximal end of the optical fiber and conveyed through the fiber to the membrane causing the pH sensitive dye to react, and light is thereafter conveyed back through the fiber with an intensity indicative of blood pH level. The oxygen sensitive dye also is caused to fluoresce, and transmit readable fluorescence via the oxygen quenchable dye which varies with oxygen partial pressure.

Therefore, the invention of the '814 patent provides a fiber optic sensitive probe for sensing both pH and oxygen partial pressure, either simultaneously or in sequence, which is made possible by the employ of the composite membrane. As also described in this patent, the hydrophilic membrane containing the pH sensitive dye and the hydrophobic microspheres contained in the membrane which contain the oxygen quenchable dye, i.e. the two measurement vectors, can be admixed with one another the mixture deployed at the same time in the same probe to obtain their respective measurements.

In U.S. Pat. No. 5,127,405, another version of a fiber optic probe is described in which, inter alia, specialized light collecting and processing equipment is employed at one end of an optic fiber and a probe is employed at the other end for insertion into the body. This is described as an oxygen-permeable transport resin in which is embedded a luminescent composition comprising crystals of an oxygen quenchable phosphorescent material. Response light from the fiber optic probe is processed in the detection equipment by derivation of frequency domain representation, and characteristics of the frequency domain are thereafter employed to derive values for luminescence lifetimes or decay parameters, which are corrected into values of conditions to be monitored.

U.S. Pat. No. 4,752,115 also discloses an oxygen sensing device which employs an optical fiber, 250 nm in diameter or small enough for insertion into veins and/or arteries, and in which one end is coated with an oxygen sensitive (oxygen quenchable) fluorescent dye which fluoresces light back, dependant upon regional oxygen partial pressure, to the other end which is adapted to receive the fluorescent light and provide an outlet for the light to go to a signal detector to provide oxygen measurement. The oxygen sensing end is made by dipping an end of the optical fiber into a solution containing an oxygen sensitive fluorescent dye, such as, tris (4, 7-diphenyl-1, 10-phenanthroline) Ru(II) perchlorate, a carrier polymer, such as, polyvinyl chloride and a plasticizer dissolved in, for example, THF. The plasticizer is said to be necessary for a fast response and high sensitivity. The oxygen sensing end can also include a gas-permeable sleeve about the optical fiber (FIG. 1, element 32).

Another fluorometric oxygen sensing device is described in U.S. Pat. No. 5,012,809 which employs a fluorometric sensor constructed with silicone polycarbonate bonded to one or more plastic fiber optic light pipes using polymethylmethacrylate glues.

U.S. Pat. No. 4,476,870 discloses a fiber optic probe for implantation in the human body for gaseous oxygen measurement in the blood stream. The probe employs oxygen quenchable dye fluorescence, and uses two 150 um strands of a plastic optical fiber which end in a tubular envelope packed with fluorescent light-excitable dye placed on a porous absorptive particulate polymeric support. The tubular envelope is made of a hydrophobic, gas-permeable material.

U.S. Pat. No. 4,200,110 discloses a fiber optic pH probe employing an ion-permeable membrane envelope enclosing the ends of a pair of optical fibers, with a pH sensitive dye indicator composition disposed within the envelope.

U.S. Pat. No. 3,814,081 describes another variant of an optical measuring catheter for measuring the degree of oxygen saturation in blood using an illuminating fiber optical system and a light receiving fiber optical system, both of which are arranged along side of each of other, and both having forward ends adapted to be inserted together into the organ of a living body to detect illumination of from 600 to 750 nm to measure blood oxygen concentration. This method does not rely on oxygen quenchable phosphor/ fluorphor compounds, but instead employs direct measurement of light absorption of Hb vs. $HbO_2$ at specific wave lengths.

In another example, U.S. Pat. No. 3,787,119 describes a multiple photometer device mounted in a catheter, which utilizes at least two associated photosensitive cells to measure physical and chemical characteristics of blood in vivo.

SUMMARY OF THE INVENTION

In accordance with one aspect of the present invention, there is provided an improved optical probe for use in measuring blood and tissue oxygen partial pressure (concentration), and in another aspect, the improved probe allows for both oxygen and pH ($CO_2$) measurements.

In its broadest sense, the invention provides a device for tissue and blood oxygen measurement and/or pH ($CO_2$) measurement in humans and animals, which comprises fiber optic means effective for transmitting phosphorescent and/or fluorescent light, an oxygen and/or pH probe means situated at one end of the fiber optic means which comprises a portion of the fiber optic means enclosed by a gas-permeable membrane, a reservoir means which comprises a solution of an oxygen-quenchable phosphorescence emitting compound and/or fluorescence emitting compound situated between the gas permeable membranae and fiber optic means, and further comprising at the other end of the fiber optic means a phosphorescent and/or fluorescence light dectection means to receive light from the fiber optic optic means and to measure tissue and blood oxygen and/or pH and further comprising an excitation light emitting means to provide light to the phosphorescent and/or fluorescent emitting compounds.

In a preferred embodiment, the oxygen-quenchable phosphorescence emitting compound and/or fluorescence emitting compound (hereinafter "phosphor" and "fluophor" respectively) is dissolved in a solvent having substantially the same refractive index as the fiber optic means.

In another preferred embodiment, the fiber optic means portion comprising the probe means has at least a portion thereof etched or is otherwise provided with a plurality of grooves or depressions to provide additional angled surfaces to aid in scattering excitation light outward into the phosphor and/or fluorophor containing medium to the fiber optic means, and thereafter back to the light detection means.

In yet a further embodiment of the invention, the probe means contains a plurality of grooves or depressions, a portion of which contain an oxygen-quenchable phosphor for oxygen measurement and a portion of which contain a fluorophor for pH ($CO_2$) measurement.

DETAILED DESCRIPTION OF PREFERRED EMBODIMENTS

The foregoing and other embodiments and advantages of the present invention will become more readily apparent from the following detailed description of preferred embodiments.

Figure 1:
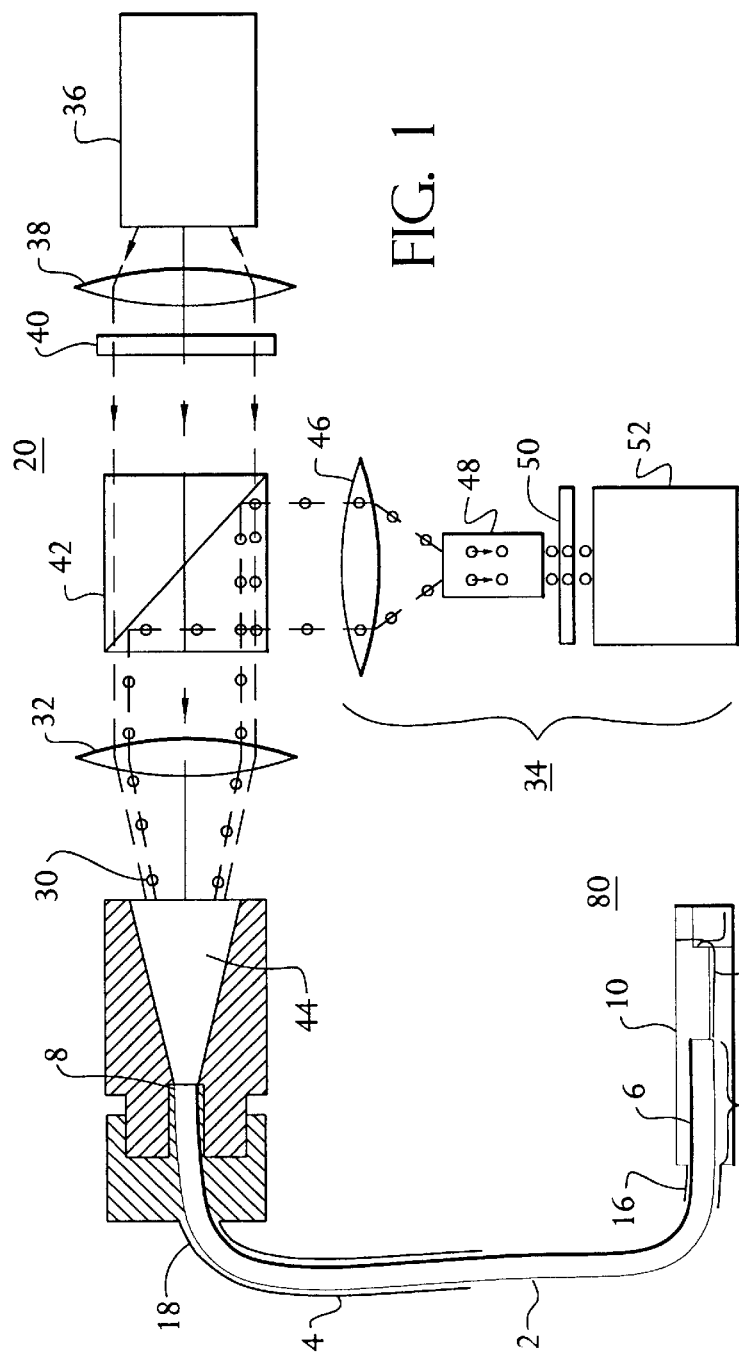
FIG. 1 is a schematic cutaway view of a preferred embodiment of an oxygen partial pressure measurement apparatus of the invention.
Figure 2:
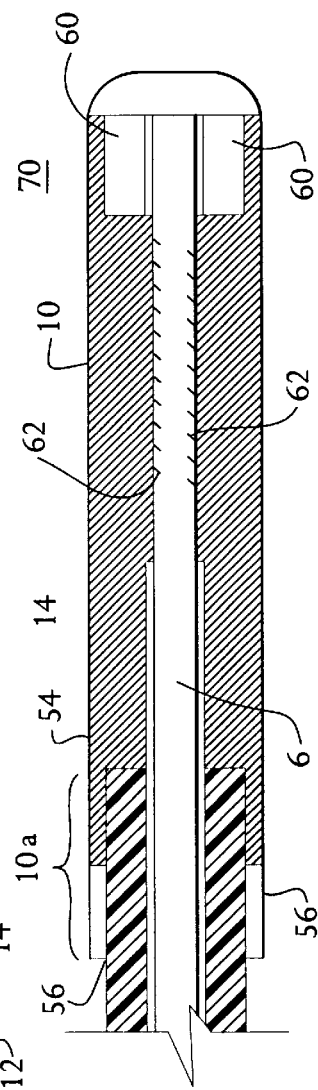
FIG. 2 is an enlarged schematic cutaway view of a preferred probe means for use in the apparatus and process of the invention, such as exemplified in FIG. 1.
Figure 3:
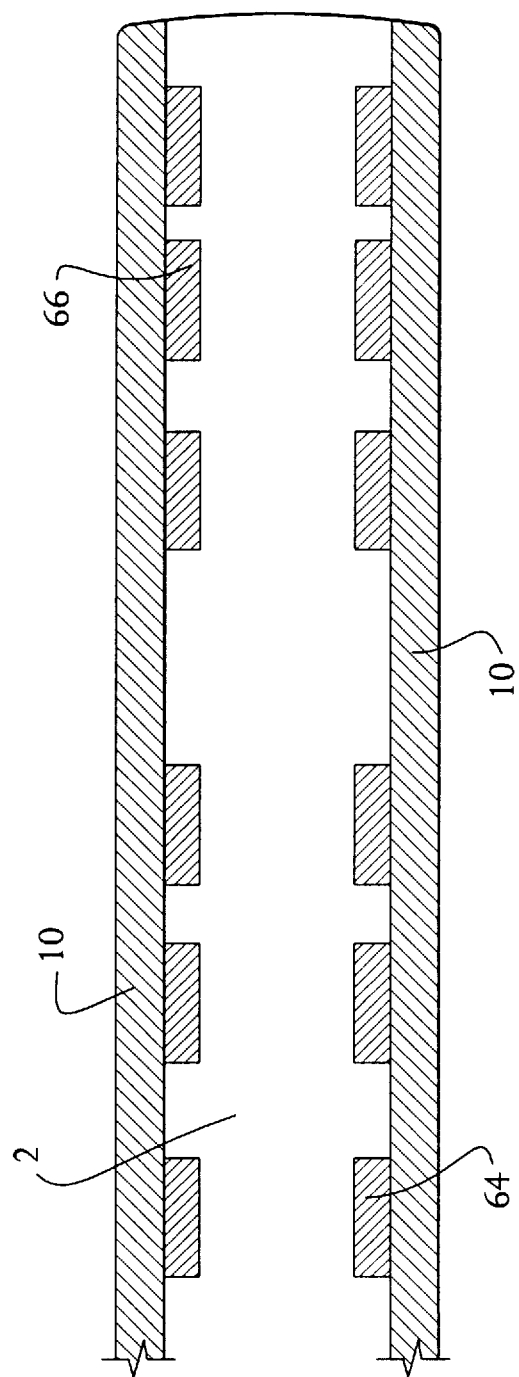
FIG. 3 is an enlarged schematic cutaway view of another preferred probe means for use in the apparatus and process of the invention, such as exemplified in FIG. 1.

Reference is made to preferred embodiments exemplified in FIGS. 1–3, which are intended for purposes of illustration only, and are not intended in any way to limit the scope or spirit of the invention defined by the claims.

In FIG. 1 there is illustrated an example of apparatus of the invention as applied to the measurement of oxygen partial pressure in a patient's tissue or within a blood vessel, which includes an optical fiber means 2, which can extend through an elongated lumen catheter means 4, and which optical fiber means has a distal end 6 and a proximal end 8, with the catheter means also having distal and proximal ends 16 and 18, respectively. The optical fiber means distal end 6 forms part of a probe means designated generally as 70 which is adapted to be inserted into a patient's blood vessel and advanced to a site at which the desired measurements can be made.

A gas permeable film means 10, for example, an oxygen-permeable membrane, discussed in greater hereinbelow, encloses a portion 12 of the distal end 6 of the optical fiber means 2, to enclose and form a reservoir 14 of a solution of an oxygen-quenchable phosphorescent compound and/or a fluorescence emitting compound, respectively, both of which are discussed in greater detail hereinbelow. Thus, as shown in FIG. 1 the optical fiber means 2 forms a core optic means of the catheter, with the distal end 6 of the optical fiber means 2 extending beyond the catheter means distal 16. It is contemplated that the optical fiber means 2 may be carried by the catheter means 4 during insertion into a blood vessel, or the distal end 6 of the optical fiber means may be inserted and advanced through the catheter 4 lumen, for example, in a blood vessel.

The catheter means proximal end 18 with core proximal end 8 of fiber optic means 2 leads to a light source detector means designated generally as 34. As is known, with the optical probe in place for oxygen measurement (and/or pH measurement), a light source 30 can be energized to provide the desired wavelength, for example, using a suitable filter means to cause the phosphor to emit phosphorescent light (and/or fluorphor to emit florescent light) at a desired wavelength with oxygen partial pressure (and/or pH) measured in detector means 34 by the phosphorescence lifetime or of the phosphor or fluorescense lifetime of the fluorphor, with emitted light quenched or diminished by oxygen. A discussion of fluorescense and pH measurement is described more fully hereinbelow.

The preferred light source is light emitting diodes ($LED_s$), preferably monochromatic light sources, which are readily modulated and have desirable intensity. With respect to partial pressure oxygen measurement, a sine wave signal of the desired frequency can be generated by a digital signal processor (DSP) system for digitizing and quantifying a phosphorescence signal, including determination of a phase shift relative to the light output of the LED and of the phosphorescence signal magnitude. The signal can be generated using a 16 bit DAC, (digital to analog converter) and smoothing circuits of stereo codec. This signal is used to control the current in the LED driving circuit. The LED driver circuit is preferably designed to provide greater than 90% modulation of light output by adding a DC signal to the sinusoidal signal such that the minimum current is just above minimum current is just above threshold for light emission. Above this threshold light output is nearly a linear function of the current through the LED.

Generally, in a preferred embodiment for carrying out this invention, light from $LED_s$ will pass through interference filters combined with a dichroic beam combiner, and focused on one branch of a bifurcated light guide to provide excitation light. The interference filters are used to block the long wavelength ("tail") in the emission of the LED, which might interfere with fluorescence measurements. The separation of excitation and emissions wavelengths of oxygen-quenchable phosphors is generally sufficient to not require such a filter.

In a further preferred embodiment, a mechanical adaption can be constructed which optimizes assembly of the LED, interference filter and of an optical filter fibrous light guide, which can be connected to a fiber optic switch to send the beam either to a catheter containing optic fiber means as either or both excitation for the phosphor and/or fluorphor, or to a photodiode detector to measure relative intensities of fluorescence excitation at two wavelengths. In the preferred configuration, the pH ($pCO_2$) would be measured by the response of a fluorescent indicator which fluoresces at the same wavelength but absorbs at different wavelengths in the acid and base forms. This allows the ratio of the fluorescence at the two different excitation wavelengths to be used as a measure of the pH. As long as the relative intensities of excitation light of the two different wavelengths is known, the measured pH values are independent of the concentration of fluorophor, the intensity of the excitation light, and the efficiency of collection of the emitted fluorescence. The measured excitation energies will be used to correct the fluorescence intensity ratio for that for equal energy of the two wavelengths. After switching, excitation light can be passed into a 50:50 coupler with a common end terminated with a connector designed for rapid and reproducible connection of a fiber optic means, for example, which is situated in a catheter means.

Photodiodes with internal amplifiers can be selected for the optimal light sensitive surface area and lowest noise level. For example, Model No. OPT202 by Burr-Brown is particularly suitable for use in this invention since it has an appropriate surface area (more than 5 mm$^2$) and excellent photosensitivity, about 500 mV/uW for the 500 to 950 nm wavelength range. The signal from the photodiode will be further amplified with an AC-coupled operational amplifier. The quality of the phase detection depends on the reduction of noise level in the photodiode output signal. After amplification, the photodiode output signal is delivered to the analog multiplexer, and then to the input of the 16 bit, 48 kHz Delta-Sigma ADC.

Emitted phosphorescent and/or fluorescent light, transferred from the distal end 6 to the proximal end 8 of fiber optic means 2, can be directed to a lens means 32 which is suitable for passing light at a desired wavelength, for example, on the order of about 500 to about 1,000 nm, and which in turn is detected by detector means 34, thereby providing an output indication which represents the partial pressure of oxygen and/or pH in the area of the patient tested.

Preferably, emitted phosphorescence and/or fluorescence is collected by the fiber optic means 2 in the catheter and transferred to the common end of a bifurcated fiber in communication with the aforesaid coupler, wherein 50% of the signal is passed into a branch returning to the detector means. After it is carried to the detector means, it can be passed through an interference filter to remove excitation light for measurement. The light can be measured either with a silicon photodiode containing a preamp or a photomultiplier. The photodetector output is amplified to provide a signal of the voltage which is optimal for the ADC (analog to digital converter). Preferably, the instrument can time share and measure phosphorescence and fluorescence independently. Generally, in this preferred embodiment, individual measurements will each desirably require at most about 1–2 seconds with the phosphorescent excitation light turned off during fluorescence measurements and vice versa. In a more preferred embodiment, two different detectors for fluorescence and phosphorescence measurement is employed, wherein a return fiber optic switch is placed in a return light path and used to switch between the two detectors.

Software routines for use with the present invention can include the following: generation of the sinusoidal signals for controlling the LED light output for both fluorescence and phosphorescence excitation; for collecting and storing the digitized photodetector output including signal averaging, calculation of phase shift (phosphorescence) and magnitude (phosphorescence and fluorescence), oxygen pressure and pCO$_2$(pH).

Data processing routines can include digital filtering, averaging in the time domain, and phase shift recovery in the frequency domain. The frequency domain representation of the data can be obtained by the application of Fast Fourier Transform algorithms.

The fiber optic means 2 can be of any construction known in the art, and is not critical to practice of the invention. It can, for example, be a plastic light guide such as polymethylmethacrylate, or a silica light core which is of a size suitable for entry into an area to be tested, such as a vein, which normally is in the 300–500 um diameter range.

The phosphor employed in this invention is preferably a material having:

(1) a substantial sensitivity to oxygen, i.e. phosphorescence with high quantum yields at room temperature ($\geq 2\%$); and (2) a suitable phosphorescent lifetime, preferably on the order of from about 0.1 to about 1 m sec.

A new class of phosphors suitable for oxygen measurements which have the above desirable qualities is now available, and are preferably used as the phosphors of choice in this invention in reservoir means 14 shown in FIG. 1. These phosphors are described in detail in Vinogradov et al., *Metallotetrabenzoporphyrins. New Phosphorescent Probes for Oxygen Measurements*, J. Chem. Soc., Perkin trans. 2:103–111 (1995) and in copending application Ser. No. 08/137,624, filed Oct. 15, 1993, the entire disclosures of which are incorporated herein by reference. These phosphors are metallo complexes of, for example, extended porphyrins, such as Pd or Pt tetrabenzoporphyrins (PdTBP) tetranaphthaloporphyrins (PdTHP), and tetraphenyltetrabenzoporphyrins (PdTPTBP) and derivatives thereof, which are preferred for use in this invention. These compounds can be represented by the general formula,

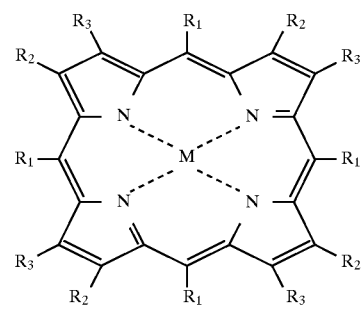

where $R_1$ is substituted or unsubstituted aryl; $R_2$ and $R_3$ are independently hydrogen or are linked together to form substituted or unsubstituted aryl; and M is $H_2$ or a metal.

As is apparent to those skilled in the art, when $R_2$ and $R_3$ are linked together to form an aryl system, the aryl system is necessarily in a fused relationship to the respective pyrrole substrate.

M is preferably a metal selected from the group consisting of Zn, Al, Sn, Y, La, Lu, Pd, Pt and derivatives thereof. Non-limiting examples of suitable metal derivatives include LuOH, YOH, AlOH and LaOH.

In certain preferred embodiments, the compounds of the present invention are tetrabenzoporphyrin (hereinafter "TBP") compounds, which correspond to the compound of formula I above wherein vicinal $R_2$ and $R_3$ groups are linked together to form benzene rings which are fused to the respective pyrrole rings. Also preferred are tetranaphthoporphyrin (hereinafter "TNP") and tetraanthraporphyrin (hereinafter "TAP") compounds wherein vicinal $R_2$ and $R_3$ groups are linked together to form naphthalene and anthracene ring systems, respectively. As with the fused benzene rings, the naphthalene and anthracene ring systems are fused to the respective pyrrole rings.

Unless indicated otherwise, or unless apparent from the disclosure, further references herein to "TBP" compounds is understood to refer also to TNP and TAP compounds.

Preferred TBP compounds have the following formula

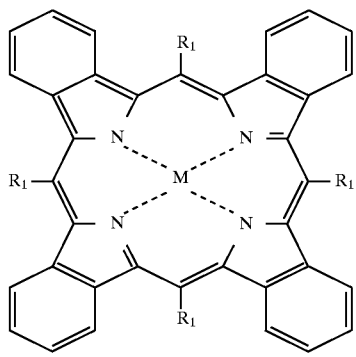

(II)

wherein $R_1$ and M are as defined above. Particularly preferred TBP compounds are metallotetrabenzoporphyrin (hereinafter "MTBP") compounds where M is a metal or metal derivative as described hereinbefore.

TBP compounds of formula IV above can be synthesized, for example, by template condensation of potassium phthalimide with sodium acetate (or sodium phenylacetate) in the presence of zinc acetate (See, for example, V. N. Kopranenkov et al., *J. Gen. Chem.* (*Russ*), Vol. 51(11), pp. 2165–68 (1981) and V. N. Kopranenkov et al., *J. Org. Chem. of USSR*, Vol. 15(3), pp. 570–75 (1979)) as described in the following equation:

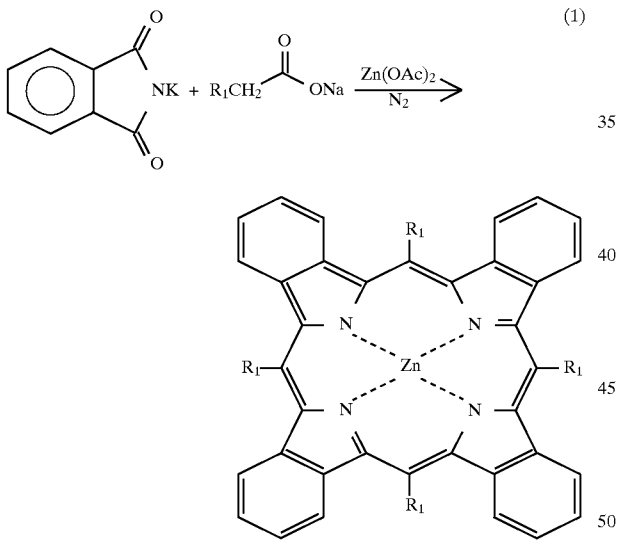

(1)

where $R_1$ is defined as above. The reaction mixture is preferably heated to a substantially elevated temperature, for example, about 360° C., for about 40 minutes. Zinc acetate in this reaction is reportedly replaceable with Zinc benzoate. See K. Ichimura et al., Inorgan. Chim. Acta; 182:83–86 (1991).

The product from the reaction of equation 1, zinc tetrabenzoporphyrin (hereinafter "ZnTBP"), is reduced to the dihydro product by heating in a mixture of acetic and phosphoric acids as described in the following equation:

(2)

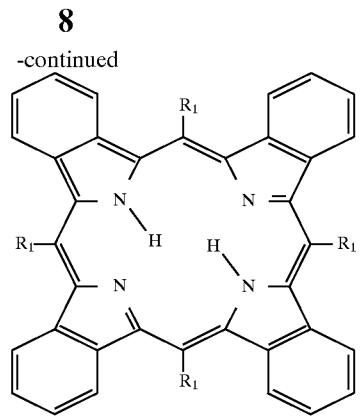

wherein $R_1$ is defined as above. Preferably, the acetic and phosphoric acids are mixed in a ratio of about 1:3 and the reaction mixture is heated to about 80° C. The reaction is substantially complete in about 2 hours.

The dihydrotetrabenzoporphyrin product from the above reaction (hereinafter "$H_2$TBP"), was purified by flash chromatography on an alumina ($Al_2O_3$) column. Metal insertion was carried out in an imidazole melt as set forth in the following equation:

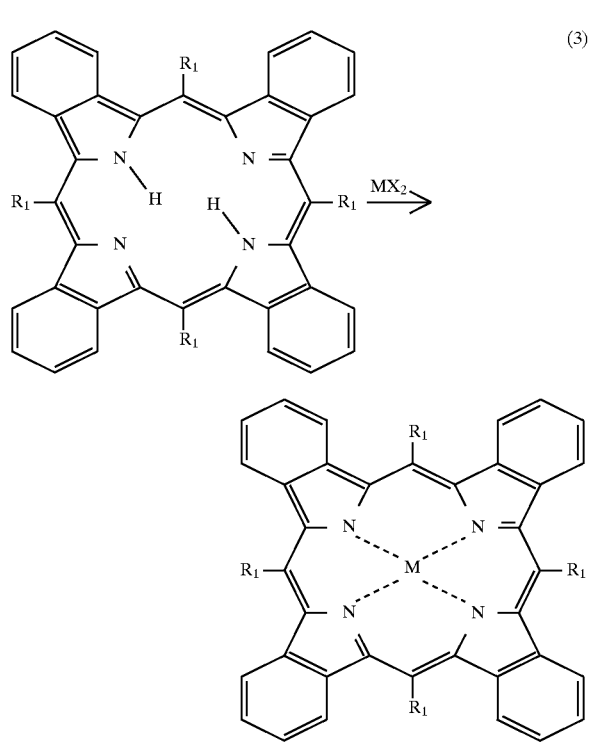

(3)

wherein $MX_2$ is a source of metal ions and preferably corresponds to chlorides, bromides and acetates of metals. Metal acetates are preferred sources of metal ions as compared to the corresponding halides. Palladium acetate (Pd(OAc)$_2$) is particularly preferred and provided 99% conversion to the metal complex in refluxing tetrahydrofuran (THF).

The reaction of equation 3 is preferably conducted at elevated temperatures, for example, temperatures greater than 100° C. Preferably, the reaction is conducted at a temperature of about 200° C., and the reaction is substantially complete after about 1 hour.

Particularly preferred among the TBP compounds are the compounds of formula IV above where at least one of $R_1$ is substituted or unsubstituted phenyl. These compounds are referred to hereinafter as phenyltetrabenzoporphyrin (hereinafter "PhTBP") compounds. Preferred PhTBP compounds include substituted or unsubstituted tetraphenyltetrabenzoporphyrin (hereinafter "TPhTBP") compounds, including mesotetraphenyltetrabenzoporphyrin (hereinafter "m-TPhTBP") compounds, which have the following formula:

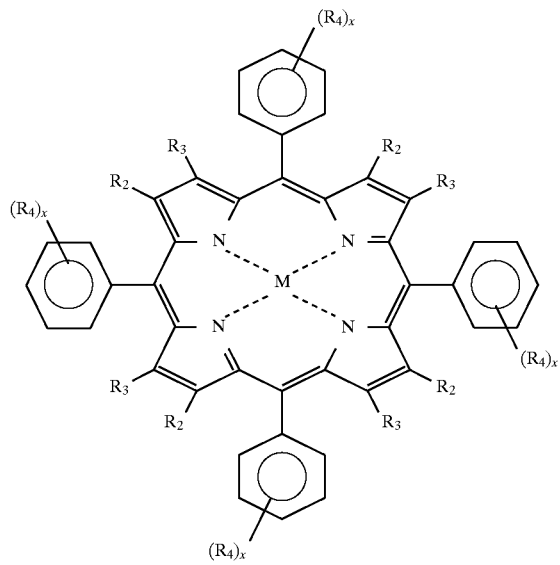

where $R_2$, $R_3$ and M are as defined above, $R_4$ is a substituent group, and x is an integer from 0 to 3. Particularly preferred TPhTBP compounds are substituted compounds of formula V where x is an integer from 1 to 3.

In connection with the preferred substituted compounds of the invention, Applicants have found that substituent groups impart desirable properties to the compounds. For example, compounds which comprise substituent groups are characterized by solubility in polar solvents, including aprotic solvents, such as dimethylformamide (DMF), acetone and chloroform ($CHCl_3$), and protic solvents, such as water. The degree of substitution and the nature of the substituent groups may be tailored to obtain the desired degree of solubility and in the desired solvent or solvent mixture.

The substituent groups are preferably substituted on the chromophobe portion of the compounds of the invention. The term "chromophobe portion" includes, for example, the atoms in the compound of formula I which are immediate to the porphyrin moiety, as well as the $R_1$, $R_2$ and $R_3$ groups. Preferably, the substituent groups do not negatively affect or alter the absorbance and/or emission characteristics of the chromophores.

Particularly preferred phosphorescent oxygen sensors for use in the method and apparatus of this invention include Pd-tetrabenzoporphyrin and Pd-meso-tetra-(4-carboxyphenyl) phosphine.

The material(s) of construction of the gas-permeable membrane is not critical to practice of the invention, and can be any of the known membranes, including but not limited to such plastic membranes as silastic, teflon, polyethylene and polypropylene.

It will be appreciated by those skilled in the art, that by enclosing the phosphor sensor molecule (and/or fluorophor) in a solution within a gas-permeable membrane, long term stability is achieved compared to conventional designs based on dyes incorporated or admixed into membranes, such as discussed above.

The designs of the light source and/or detector, in accordance with this invention, are also not critical to the practice of this invention and may take any suitable form employing any conventional and non-conventional components. In general, detector means 34 is arranged to convert light received from optical fiber means 2 into electrical signals, in which the amplitude of the electrical signals is directly related to the amplitude or intensity of incoming light, such as the quenched or diminished emitted phosphorescent light supplied to the detector, which can be, for example, a photomultiplier or photodiode. As shown in the embodiment of FIG. 1, the emitted light passes through a suitable filter means chosen so as to pass emitted light at a desired wavelength, e.g. from between about 500 nm to about 1,000 nm in accordance with the preferred phosphors of the invention. Emitted light detected by the detector means 34 provides an output indication representative of the partial pressure of oxygen.

As also shown in FIG. 1, in a preferred apparatus embodiment for carrying out the process of this invention, there is also provided a light emission means 36, such as a flash lamp or laser diodes or any other modulate light sources, which forwards emitted light preferably through a calumniating lens means 38 and thereafter through an interference filter 40 to provide excitation light, preferably in the range of from about 400 nm to about 700 nm, which thereafter travels through a dichroic beam combiner means 42 and lens means 32 through a tapered light guide 44 to optical means 2 of the light guide for exciting the phosphor compound solution in reservoir 14 of probe 70. As further shown in FIG. 1, the detector means 34 may comprise a lens means 46 for receiving emitted light from 42 along with an enlarged fiber optic light guide portion 48 (e.g. 4 mm v. ~300 ~500 um in diameter for optical light means 2) through which emitted light passes through filter means 50 to a photomultiplier means 52 (or a photodiode means, etc).

Turning now to the enlarged cutaway schematic of the probe 70 shown in FIG. 2, the optical fiber core means portion 2 can be encased with a sleeve of a suitably inert material such as a plastic for a portion thereof before and after leaving catheter 4 and entering reservoir 14 to provided greater rigidity and durability characteristics. This sleeve means is shown as 54. The membrane means 10 will preferably have a portion 10a which overlaps an end portion of catheter means 4 of a corresponding length, and in which a portion of overlap can be, for example, fusion sealed to catheter means 4, shown by seal means 56, to form a probe with membrane means 14 enclose reservoir 14. For protection and durability, the end of the probe can be reinforced with a plug or other protections means 60.

In a preferred embodiment of this invention, at least a portion of the distal end 6 of the optical fiber means 2 encased by the phosphor reservoir means 14 is configured to have a plurality of scratches, depressions, grooves, pitting or otherwise, holes and the like, shown in FIG. 2 as 62 for example, by etching of this portion of the optical fiber. As shown in FIG. 2, excitation light emanates from this fiber optic portion 6 into the phosphor solution in reservoir 14, and the resulting emitted phosphorescence due to such etching has an increased probability of being collected by the fiber for return to the detector. In effect the phosphor solution in reservoir 14, as a result of the grooves, etching, etc. becomes a part of the optical fiber means 2 itself. It has been found that it is preferred to etch a plurality of grooves around the fiber, with each groove being about a preferred 20% of the fiber diameter in depth, to allow for sufficient fiber strength, while at the same time allowing for the phosphor solution to penetrate well into the fiber. As illustrated in FIG. 2 excitation light leaving the optical fiber means 14 enters the phosphor reservoir 14 while continuing to travel nearly parallel to the fiber. Without intending to limit this invention to any particular theory, it is believed that the resulting phosphorescence lies very near and closer to the fiber than in the absence of such etching to substantially increase the probability of entering the fiber within the collection angle. Only part of the light will leave the optical fiber means 14 at each etched groove, with each additional groove adding to the total excitation and emission.

In further preferred embodiment of the invention, as show in FIG. 3, the optical fiber means 14, can contain a plurality of grooves exemplified as 64 and 66, each independently segregated from one another and encased within gas-permeable membrane means 10, to form a plurality of separate and distinct reservoir compartments. A number of these reservoir compartments can then be filled with a phosphor solution as discussed above, with a number of the thus formed reservoir compartments being filed with a suitable fluorescent pH indicator to measure pH and $CO_2$, with a substitute filter means (not shown) being employed which will pass light at a desired wavelength, for example on the order of about 500 to about 700 nm, to the detector means 34. It is also contemplated in this invention that an automated filter-changing means be employed which automatically changes with respect to a particular light source.

In similar manner to producing and collecting phosphorescent excitation light, excitation light from the optical fiber means 2 causes the fluorescence to be emitted which then passes back through the fiber optic means 2 from the distal end 6 to the proximal end 8 of fiber optic means and thereafter, inter alia, through a filter means (not shown) to the detector means 32. The intensity and/or wavelength of this light will change with the pH of the reservoir solution which provides a direct measurement of the $CO_2$ pressure in the blood outside the gas permeable membrane. This will make use of the relationship:

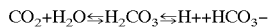

$$CO_2 + H_2O \leftrightharpoons H_2CO_3 \leftrightharpoons H^+ + HCO_3^-$$

in which the pH is a function of the $HCO_3$ in solution, $PCO_2$, and the PKa of carbonic acid ($H_2CO_3$).

Any known pH sensitive compound, such as dye, of the type which will fluoresce when excited by light is contemplated for use in this invention ("fluorphor"), such as derivatives of fluorescein with appropriate pKa values. It is also contemplated that the pH content may be measured by light absorbance, thereby employing an absorbance dye such as, for example, phenol red or brilliant yellow. It is, of course, important that a fluorphor be chosen that does not diffuse out of the gas-permeable membrane enclosing it in its respective reservoir compartment.

As discussed hereinabove, the efficiency of capturing emitted fluorescence and pH measurement in accordance with this invention is maximized by virtue of the grooved topography of the optical fiber means 14 in its distal end.

In a further preferred embodiment of the invention, the refractive index of the phosphor solution and/or fluorphor solution in reservoir means 14 encasing the portion of distal end 6 of optical fiber means 2 is chosen to be as near, or, if possible, substantially identical, to that of the optical fiber means 2, to become in effect an extension of the optical fiber means for increased efficiency of phosphorescence/florescence light transfer through the optical fiber means 2 to the detector means 32. Again without intending to limit this invention to any particular theory, it is known that optical fibers conduct light because the internal refractive index is much higher than that of the environment outside the fiber.

For example, the refractive index of air is approximately 1.0 while that of typical optical fiber is about 1.5. This difference means that the fiber collection angle is about 60°. That is, light approaching the fiber wall from the inside at angles up to 30° (½ the collection angle) is reflected back into the fiber and continues to travel along the fiber. This would also be the case for a thin tube filled with a high refractive index solution, and efficient light guides constructed in this manner are known. See, for example, Oriel Corp., Stratford, CT. There are many liquids known to possess refractive indices high enough for forming light guides, such as, for example, possessing a refractive index higher then about 1.4, several of which are exemplified in table 1 herein below.

In the case of a perfect or near perfect refractive index match, substantially all of the excitation light can be used to generate phosphorescence/fluorescence and the phosphorescence/fluorescence collection angel approaches that of the optical fiber, which can be greater than 60°.

In the practice of this preferred embodiment, the phosphor and fluorphor are dissolved in a solution with a refractive index similar to that of the optical fiber. As a result the light in the fiber will not be reflected at the fiber-solution interface but will travel through this interface and be reflected at the solution-air interface. Thus, the solution within the oxygen permeable membranae will become an integral part of "composite" light guide. Excitation will be fully optimized, since attenuation of the excitation light will occur only by absorption by the phosphors and fluorophors in the solution. Collection of the emitted light will occur at the full 60° acceptance angle of the composite (solution & fiber) optical light guide. A table refractive indices of some suitable liquids follows in table 1below:

TABLE 1*

| LIQUID | refractive index | LIQUID | refractive index |
| --- | --- | --- | --- |
| Water | 1.33 | 80% sucrose in water | 1.49 |
| 40% sucrose in water | 1.40 | glycerol | 1.47 |
| 60% sucrose in water | 1.44 | Mineral oil (parafin oil) | 1.47 |

*Communication grade acrylic fiber optics with a core refractive index of 1.495 and an acceptance angle of 60°.

We claim:

1. A detection device for tissue oxygen and/or pH ($CO_2$) measurement in animals and humans comprising fiber optics means for transmitting emitted phosphorescent and/or fluorescent light, a probe at one end of the fiber optic means comprising a portion of the fiber optic means enclosed by a gas-permeable film, and a reservoir of a liquid which contains an oxygen quenchable phosphorescence emitting oxygen sensor and/or a fluorescence emitting pH sensor situated between the gas-permeable film and the fiber optic means, and further comprising at the other end of the fiber optic means phosphorescent and/or fluorescent detecting means and excitation light emitting means.

2. The device of claim 1 wherein said sensor is an oxygen-quenchable phosphorescence emitting oxygen sensor.

3. The device of claim 2 wherein said oxygen sensor comprises an absorption band at a wavelength of greater than about 400 nm.

4. The device of claim 1 wherein said sensor comprises an emission band at a wavelength of greater than about 400 nm.

5. The device of claim 1 having absorption and emission bands located in a range from about 400 nm to about 1000 nm.

6. The detection device of claim 5 wherein said absorption band ranges from about 400 to about 700 nm.

7. The device of claim 2 wherein said sensor comprises porphyrin.

8. The detection device of claim 7 wherein said porphyrin comprises metalloporphyrin.

9. The detection device of claim 8 comprising an oxygen sensor compound which is capable of phosphorescing and which has the formula:

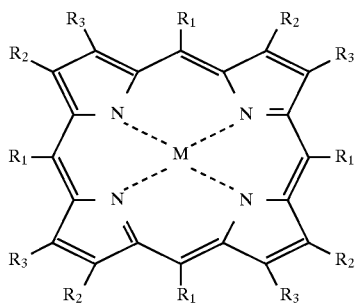

wherein:
$R_1$ is substituted or unsubstituted aryl;
$R_2$ and $R_3$ are independently hydrogen or are linked together to form substituted or unsubstituted aryl; and
M is $H_2$ or a metal.

10. The detection device of claim 9 wherein the oxygen sensor compound M is a metal selected from the group consisting of Zn, Al, Sn, Y, La, Lu, Pd, Pt and derivatives thereof.

11. The detection device of claim 10 wherein said derivatives comprise LuOH, YOH, LaOH or AlOH.

12. The detection device of claim 9 wherein $R_2$ and $R_3$ of the oxygen sensor compound are linked together to form an aryl system.

13. The detection device of claim 12 wherein said aryl system comprises phenyl, naphthyl or anthryl.

14. The detection device of claim 13 wherein $R_1$ comprises substituted phenyl.

15. The detection device of claim 14 wherein said substituted phenyl comprises Pd-meso-tetra-(4-carboxyphenyl) porphine.

16. The detection device of any of claims 1–15 in which said portion of said fiber optic means enclosed by said gas permeable film contains one or more grooves.

17. The detection device of any of claims 1–15 in which the refractive index of said reservoir liquid is near that of said fiber optic means.

18. The detection device of claim 16 in which the refractive index of said reservoir liquid is substantially identical to that of the fiber optic means.

19. The detection device of any of claims 1–15 wherein said portion of said fiber optic means enclosed by said gas permeable film contains at least two or more grooves, and wherein at least a portion of the grooves contain oxygen quenchable phosphorescence emitting oxygen sensor and a portion contains a fluorescence emitting pH sensor.

20. The detection device of claim 19 wherein the refractive index of said liquid is near that of said fiber optic means.

21. The detection device of claim 20 wherein the refractive index of said liquid is substantially identical to that of the fiber optic means.

22. A method for tissue oxygen measurement and/or pH measurement in animals and humans with the device of claim 1, comprising:

contacting a subject with said probe;

emitting excitation light from said emitting means into said fiber optic means;

detecting phosphorescent and/or fluorescent emissions from said oxygen quenching and/or fluorescence emitting pH sensor with said detecting means; and measuring tissue oxygen and/or pH based on results of said detecting step.

* * * * *